United States Patent [19]

Ferruti et al.

[11] 4,223,011
[45] Sep. 16, 1980

[54] THERAPEUTIC COMPOSITIONS CONTAINING POLYMERS HAVING POLYUNSATURATED ACID RADICALS

[76] Inventors: Paolo Ferruti, V.le Cassiodoro, 24; Rodolfo Paoletti, V.le Regina Margherita, 43, both of Milano, Italy

[21] Appl. No.: 18,986

[22] Filed: Mar. 9, 1979

Related U.S. Application Data

[60] Division of Ser. No. 737,546, Nov. 1, 1976, Pat. No. 4,145,320, which is a continuation-in-part of Ser. No. 622,441, Oct. 14, 1975, abandoned.

[30] Foreign Application Priority Data

Oct. 15, 1974 [IT] Italy .................. 28419 A/74

[51] Int. Cl.$^2$ .................. A61K 31/78; C08L 91/00
[52] U.S. Cl. .................. 424/81; 260/23 AR; 525/329
[58] Field of Search .................. 260/824 R; 424/81

[56] References Cited

U.S. PATENT DOCUMENTS 3,897,513   7/1975   Sundet .................. 260/824 R
4,145,320   3/1979   Ferruti et al. .................. 424/81

OTHER PUBLICATIONS

M. Dino et al., J. Am. Chem. Soc. 1964, pp. 23-26, vol. 37, No. 1.
N. A. Plate et al., J. Polymer Sci. Part C, No. 22, pp. 547-568, (1969).
Y. Imanishi et al., J. of Polymer Science Part A, vol. 3, pp. 2455-2474, (1965).
J. Rehner, Jr. et al., J. of Polymer Sci., vol. 11, No. 1, pp. 21-36.

*Primary Examiner*—Delbert R. Phillips
*Attorney, Agent, or Firm*—Stevens, Davis, Miller & Mosher

[57] ABSTRACT

A polymer having a molecular weight between 1,000 and 1,500,000 characterized in that it contains the radical of a polyunsaturated acid selected from the group consisting of 8,11,14-eicosatrienic acid, 5,8,11,14-eicosatetraenoic acid, and 5,8,11,14,17-eicosapentenoic acid, bound to a macromolecular backbone of polyacrylic or polymethacrylic units through oxyalkylenic, aminoalkylenic or oxyaminoalkylenic chains.

4 Claims, No Drawings

THERAPEUTIC COMPOSITIONS CONTAINING POLYMERS HAVING POLYUNSATURATED ACID RADICALS

This is a division of application Ser. No. 737,546 filed Nov. 1, 1976, now U.S. Pat. No. 4,145,320 which in turn is a continuation-in-part of application Ser. No. 622,441, filed Oct. 14, 1975, now abandoned.

The present invention refers to new polymers characterized by the presence of polyunsaturated acid radicals with 20 carbon atoms bound to the polymeric matrix in such a way to be hydrolized in biological systems while forming prostaglandins. More precisely, the present invention concerns high polymers containing radicals of the eioosatrienoic, eicosatetraenoic, or eicosapentenoic acids bound to the macromolecular matrix by ester or amide bonds, which radicals ar gradually hydrolyzed in a predetermined way in biological systems and contemporaneously cyclized to give free prostaglandins.

It is well known that prostaglandins represent one of the most interesting developments in the biomedical field during last years.

From the chemical point of view prostaglandins are essentially polyunsaturated hydroxy acids with a skeleton of 20 carbon atoms partially cyclized to form a ring of 5 carbon atoms. Prostaglandins have been classified in several series of which two have significant biomedical effect. These two major series differ only because one (PGF) contains the hydroxyl groups in the 5 carbon atom ring, and the other (PGE), a keto group and a hydroxyl group in the same ring. Subclasses are also known characterized by the presence of a double bond in a fixed position or by the presence of more than one double bond. In all cases prostaglandins present a carboxyl and at least one hydroxyl group free to react.

Prostaglandins are formed in the body starting from long-chain polyunsaturated fatty acids, essentially 8, 11, 14-eicosatrienoic acid, 5, 8, 11, 14-eicosatetraenoic acid, and 5, 8, 11, 14, 17-eicosapentenoic acid, released by specific enzymatic reactions from tissue lipids.

According to recent studies, prostaglandins are responsible in the organism for a great variety of physiological and pharmacological effects, from fertility control to stimulation of smooth muscle contraction, regulation of arterial pressure, platelets, aggregatior, gastric secretion.

From the practical point of view, a considerable body of published evidence demonstrates that prostaglandins are of use to solve the problem of birth control, as preventing agents if administered at appropriate time and doses, or by inducing abortion.

However, the great hopes in this field have been partially non-substantiated by a practical use of prostaglandins, due to the insurgence of collateral effects which cannot be eliminated or controlled. For example, in order to obtain the desired effect of fertility control or abortion induction, prostaglandins should be given at such large doses and for such prolonged periods, that other biological effects of prostaglandins become evident, as the induction of hypotensive or hyppertermic crisis, intestinal smooth muscle contractions and thus vomit and diarrhea, headache, decrease of the pain treshold in muscles and articulations and platelets aggregation.

We have unexpectedly found that new polymers may be synthetized containing the radicals of the polyunsaturated acids precursors of prostaglandins in the organism bound to the macromolecular matrix by covalent bonds of esteric or amidic type.

Such polymers in biological systems are gradually hydrolysed releasing predetermined amounts of acids during predetermined time intervals, which acids are immediately transformed by the organism to prostaglandins.

Such polymer classes are non-toxic for mammalian organisms, give rise to non-toxic metabolites and can be predesigned from the point of view of the chemical nature, of the molecular weight, of the percentage of acid radicals contained in the macromolecular complex and of the type of chemical bonds through which these radicals are bound to the macromolecular matrix. This may be done in such a way to insure the presence of blood and tissues of strictly controlled concentrations of prostaglandins for the desired time intervals.

The presence in excess prostaglandins is therefore avoided and undesirable side effect due to prostaglandins and/or to their metabolites can be prevented or strongly reduced.

Our new polymers are characterized by a polyvinyl backbone to which said polyunsaturated acid radicals are bound by covalent, esteric or amidic bonds through appropriate side chains.

Preferably the fundamental polyvinylic structure is a polymer of acrylamide, methacrylamide, acrylic acid or methacrylic acid.

These new polymers, according to the invention, are preferably prepared by:

(a) preparation of acrylic monomers containing reactive groups chosen in the group consisting of 1-acryloilbenzotriazole, 1-acryloil methoxybenzotriazole, 1-acryloilmethylbenzotriazole, 1-acryloil imidazole, N-acryloilsuccinimide and N-2,4,5-trichlorophenylacrylamide; homopolymerization of these monomers or their copolymerization with different vinylic monomers; reaction of these macromolecular substances with alkylene-diamines, hydroxyalkilamines or alkylene dihydroxycompounds in order to obtain side chains containing reactive hydroxy or amminic groups; reactions of these new macromolecular substances with the polyunsaturated acids;

(b) homopolymerisation of acrylic acid or its copolymerisation with other vinylic monomers; reaction of these polymers or copolymers with carbonyldiimidazole in order to introduce reactive groups of acetylimidazolide type; reaction of these macromolecular substances with alkylene-diamines, hydroxyalkilamines or alkylene dihydroxycompounds in order to obtain side chains containing reactive hydroxyl or amminic groups; reactions of these new macromolecular substances with the polyunsaturated acids.

Acrylic polymers and copolymers containing reactive functional groups as described and successively acrylic polymers and copolymers containing side chains comprising hydroxy or amino groups, are prepared according to methods pertaining to the art and described in particular in the following publications:

(1) Encyclopedia of Polymer Science and Technology—Vol. 1, pages 177-273

(2) Polymer—1972, Vol. 13, Oct. 462-464

(3) Reactions on Polymers—Holland—Dec. 1973

(4) J. Of Polymer Science—Vol. 12—533-559 (1974)

The reactive macromolecular structure thus prepared is reacted with arachidonic acid or with di-homo-γ-linolenic acid or with 5,8,11,14,17-eicosapentenoic acid in solution in a suitable inert, anhydrous organic solvent, under inert gas atmosphere.

The reaction temperature may vary within 10° and 80° C. and the reaction time is comprised in a minimum time of 5 hours up to 72 hours.

The temperature and the time of the reaction depend of course from the basic macromolecular structure to the reacted.

The macromolecular matrix is prepared with a determined percentage of reactive groups according to the desired percentage of polyunsaturated acids in the final product. The new polymers with a fundamental polymethacrylic structure are more slowly hydrolyzed than the corresponding acrylic polymers and therefore they release more slowly the prostaglandins acid precursors thus prolonging prostaglandins biological activity and reducing their side effects.

The polymers, according to the invention may be water soluble or insoluble and can be prepared in form of hydrophylic, but water insoluble gels. If water soluble polymers are desired, hydrophylic monomers must be used, particularly monomers selected in the group comprising 1-acryloil-4-methyl piperazine, N-acryloil morpholine, N-vinylpyrolidone which copolymerise smoothly and with almost quantitative yields with the activated acrylic monomers.

The same monomers are used if hydrophylic gels are desired, but in this case difunctional comonomers are added, in the range of 0.5 to 30%, in order to obtain a crosslinked product. These difunctional monomers are preferably chosen from the group comprising divinyl-benzene or bis-acrylamides such as methylene bis-acrylamide, N,N'-bisacryloil piperazine or N,N bisacryloil N,N'-dimethylethylene diamine.

The new polymers, according to the invention, can be administered with any procedure already in use for the free prostaglandins and particularly by intravenous, intraamniotic, intrauterine or intravaginal routes. They may be administered as an aqueous solution, as a water- or oil-suspension, as a water-insoluble gel. The aqueous solutions are preferably used for parenteral or intravenous injection; the water- or vegetable oil-suspension are preferably used for oral administration, the gels are preferably used for intrauterine or intravaginal administration.

The amount of the polymer containing the unsaturated acid radicals (which are precursors of prostaglandins) to be administered, is easily determined once it has been determined how many times more active than the corresponding free prostaglandin, the polymers are.

This activity is determined with tests of the kind indicated in the following Table.

The experiments have been carried out by using anesthethized cats weighting 2.100 kg. Anaesthesia has been induced with ethyl ether and maintained with a solution of choralase and urethane (80:100) given intravenously through the femoral vein.

Then trachea and one femoral artery are cannulated for pressure registration. A baloon is introduced in the stomach for the direct registration of smooth muscle motility.

The polymer employed is that prepared in example n. 1 which for the sake of simplicity we indicate only with (A).

This polymer contains the radicals of arachidonic acid which is the precursor in the organism of the prostaglandin $PGF_{2\alpha}$.

Thus, in order to make it possible a comparison we have not indicated the amount of polymer administered (which on the other hand is immediately deduced from the percentage of arachidonic acid therein contained) but the amount of prostaglandin $PGF_{2\alpha}$ which would form therefrom in the organism. In the Table the decrease in arterial pressure is an index of "intensity" of action, while the duration of activation of stomach motility is an index of "duration" of action. Both these are primary, positive effects of prostaglandins.

The duration of bronchospam is on the contrary an index of the undesired side-effects.

| Treatment i.v. | Dose mg/kg | Mean arterial pressure (decrease in % in mmHg) | Activation of stomach motility (duration in minutes) | Broncho spasm* (duration in sec.) |
|---|---|---|---|---|
| $PGF_{2\alpha}$ | 1 | 63 | 42 | 36,17 |
| Polymer A (corresponding to free $PGF_{2\alpha}$) | 0,375 | 63 | 112 | 18,45 |
| Polymer A (corresponding to free $PGF_{2\alpha}$) | 0,750 | 53 | 172 | 18,52 |
| Polymer obtained before the reaction with $PGF_{2\alpha}$ acid precursor | 12.135 | 0 | 0 | 0 |

*Reduction of air flux

The reported data show that by causing the formation of prostaglandins directly in the organism, through administration of high polymers containing radicals of polyunsaturated acids which are prostaglandins precursors, and controlling through the releasing of the acids radicals the amounts and the administration time of prostaglandins, it has become possible:

(a) to produce an effect three times more intense than with free prostaglandin (the same effect is produced with 0.375 mg of $PGF_{2\alpha}$ rather than with 1 mg), (b) to produce an effect three times more prolonged with doses of equivalent activity, (c) to strongly reduce side-effects. Side effects do not increase at increasing doses.

From (a) and (b) it is deduced that the polymer (A) is nearly nine times more active than the free prostaglandin formed in the organism from the arachidonic acid therein contained, since we can achieve a nearly 3 times more prolonged effect with 1/3 of dose.

Generally speaking it can be said that the polymers of the invention are from 5 to 50 times more active than the corresponding free prostaglandin, considering always as "activity", the dureation in the time of an effect of given intensity.

Besides the advantage of "activity" the new polymers present the advantage with respect to prostaglandins that, should an unforeseen or toxic effect arise in the human organism, it may be blocked at any moment by blocking transformation of polyunsaturated acids (precursors) into prostaglandins by means of specific inhybitors of prostaglandins such as for example acetylsalicylic acid, indomethacine and the like.

Moreover it has to be noted that while a prostaglandine may be put at disposal of the physician as a drug hydrosoluble or liposoluble or as a gel, with the new polymers according to the invention the same prostaglandin may be produced in the organism while administering it in any desired and suitable form only modifying the macromolecular structure to which the polyunsaturated acid (precursor) is bound. It is thus possible to use the same prostaglandin in the most different pathologic situations, both acute and cronic, and in whatever part of the organism they arise.

EXAMPLE 1

(a) A mixture consisting of 1 g of 1-acryloilbenzotriazole, 9 g of 1-acryloil-4-methyl-piperazine, 100 mg of azodiisobutylonitrile and 50 ml of anhydrous dioxane is heated at 60° C. over 40 hours, under argon atmosphere.

The reacted mixtured is poured into one liter of anyhydrous ethylic ether and a polymer separates, with nearly 100% yield, which contains 10% by weight of acryloilbenzotriazole.

(b) 1 g of the above copolymer is dissolved in 10 ml anhydrous, alcohol-free chloroform. To this solution, a solution of N,N-dihydroxyethyl-1,3-diaminopropane (0.25 g) in 2.5 ml chloroform is added. The reaction mixture is left at room temperature for 24 hours with occasional shaking. The product is then isolated by pouring the reaction mixture into 200 ml of anhydrous ether. The precipitate is collected, dissolved in chloroform (25 ml), the solution again poured into 300 ml of dry ether, and the precipitated product collected and dried at room temperature and 0.01 mmHg. The yield is practically quantitative.

(c) A solution of the above product (0.5 g) in dry, alcohol-free chloroform (2.5 ml) is prepared (solution a).

Arachidonic acid (0.2833 g) is dissolved in dry, alcohol-free chloroform (2.5 ml), and N,N-carbonyldiimidazole (0.119 g) added to this mixture (solution b).

The solution (b) is left at room temperature for 1 hour, with occasional shaking and then the solution (a) is added to it under stirring; the resulting mixture is left at 60° C. for 24 hours under indert gas atmosphere. The product is then isolated by pouring the reaction mixture into an excess of dry ether. The precipitate is collected, washed with ether and dried at room temperature and 0.001 mmHg. A practically quantitative yield of a copolymer containing 14.6% by weight of arachidonic acid which could be entirely released in biological environments, is obtained.

EXAMPLE 2

The same procedure was followed as in the previous case, but di-homo-γ-linoleic acid was substituted for arachidonic acid. The product was isolated in the same way, and it contained about 14.4% by weight of di-homo-γ-linolenic acid. The yield was practically quantitative.

EXAMPLE 3

(a) Starting from 2 g of 1-acryloylbenzotriazole and 8 g of 1-acryloil 4-methyl piperazine, and following the same procedure as described in the example 1 (a), a copolymer was prepared containing 20% by weight of 1-acryloilbenzotriazole units.

(b) 5 g of the above copolymer were dissolved in 50 ml of anhydrous dimethylformamide. Ethanolamine (0.353 g) was then added, and the reaction mixture was stirred at room temperature for 24 hours (solution a). Di-homo-γ-linolenic acid (1.595 g) was dissolved in ahydrous dimethylformamide (5 ml) and to this solution, 0.936 g of N,N'-carbonyldiimidazole were added under vigorous stirring. The solution was then stirred for 1 hour at room temperature (solution b).

Solutions (a) and (b) were then admixed, and left at 60° C. for 24 hours with occasional stirring. The reaction mixture was poured into an excess of ether, and the precipitate was filtered or centrifuged, dissolved in chloroform and reprecipitated in ether to give about 5.5 g of a product containing 10.2% of di-homo-γ-linolenic acid which could be entirely released in a biological environment.

EXAMPLE 4

Exactly reproducing the preparation method described in Example 1, copolymers have been prepared containing various percentages of hydrolyzable arachidonic acid, starting from acrylic copolymers containing corresponding percentages of 1-acryloilbenzotriazole.

EXAMPLE 5

Following the procedure described in Example 2, copolymers have been prepared containing various percentages of hydrolyzable di-homo-γ-linolenic acid, starting from acrylic copolymers containing corresponding percentages of 1-acryloilbenzotriazole.

We claim:

1. A therapeutic composition containing a therapeutically effective dose of a non-toxic polymer having a molecular weight between 1,000 and 1,500,000 characterized in that it contains the radical of a polyunsaturated acid selected from the group consisting of 8,11,14-eicosatrienoic acid; 5,8,11,14-eicosatetraenoic acid; and 5,8,11,14,17-eicosapentenoic acid, bound to a macromolecular backbone of polyacrylic or polymethacrylic units through oxyalkylenic, aminoalkylenic, or oxyaminoalkylenic chains, said polymer containing units of the formula

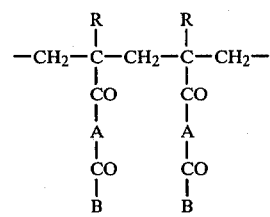

wherein R is H or CH$_3$, A represents an alkylene radical terminated at its ends with an —NH— group or an —O— group, and B represents a radical of such polyunsaturated acid sans a carboxylic group and a pharmaceutically acceptable carrier.

2. The therapeutic composition of claim 1 wherein said alkylene radical is derived from the compounds selected from the group consisting of N,N-dihydroxy ethyl-1,3-propanediamine, ethanolamine, ethylene diamine, and ethyleneglycol.

3. A therapeutic composition containing a therapeutically effective dose of a non-toxic copolymer having a molecular weight between 1,000 and 1,500,000 characterized in that it contains the radical of a polyunsaturated acid selected from the group consisting of 8,11,14-eicosatrienoic acid; 5,8,11,14-eicosatetraenoic acid; and 5,8,11,14,17-eicosapentenoic acid, bound to a macromolecular backbone of polyacrylic or polymethacrylic units through oxyalkylenic, aminoalkylenic, or oxyaminoalkylenic chains, said polymer containing units of the formula

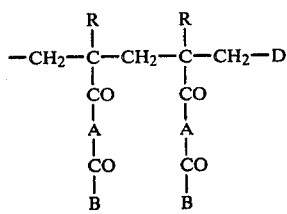

wherein R is H or CH₃, A represents an alkylene radical terminated at its end with an —NH— group or an —O— groups, B represents a radical of such polyunsaturated acid sans a carboxyl group, and D represents a divalent radical supplied by a comonomer selected from the group consisting of 1-acryloyl-4-methyl piperazine, N-acryloyl morpholine, N-vinyl pyrrolidone, divinylbenzene, methylene bis-acrylamide, N,N'-bisacryloyl piperazine, and N,N-bisacryloyl N,N'-dimethylethylene diamine and a pharmaceutically acceptable carrier.

4. The therapeutic composition of claim 3 wherein said alkylene radical is derived from the compounds selected from the group consisting of N,N-dihydroxy ethyl-1,3-propanediamine, ethanolamine, ethylene diamine, and ethyleneglycol.

* * * * *